United States Patent [19]

Goldstein

[11] Patent Number: 4,981,145

[45] Date of Patent: Jan. 1, 1991

[54] METHOD AND APPARATUS FOR DETERMINING SEBUM PRODUCTION FOR SELECTION OF COSMETICS OF COMPLEMENTARY FORMULATION

[76] Inventor: Jay A. Goldstein, 31 Claremont St., Newton, Mass. 02158

[21] Appl. No.: 426,115

[22] Filed: Oct. 24, 1989

[51] Int. Cl.$^5$ .............................................. A61B 5/00
[52] U.S. Cl. .................................... 128/760; 604/312
[58] Field of Search ................ 128/760, 762; 604/289, 604/290, 303, 308, 312

[56] References Cited

U.S. PATENT DOCUMENTS

| | | | |
|---|---|---|---|
| 2,544,798 | 3/1951 | Lippmann | 604/312 |
| 3,552,929 | 1/1971 | Fields et al. | 23/253 |
| 3,906,933 | 9/1975 | Tur et al. | 128/2 |
| 4,078,656 | 3/1978 | Crane et al. | 206/223 |
| 4,329,999 | 5/1982 | Phillips | 128/760 |
| 4,381,611 | 5/1983 | Wishman | 604/312 |
| 4,532,937 | 8/1985 | Miller | 128/795 |
| 4,623,793 | 11/1986 | Hofke et al. | 250/341 |
| 4,626,247 | 12/1986 | Frankel | 604/312 |
| 4,706,676 | 11/1987 | Peck | 128/760 |
| 4,756,314 | 7/1988 | Eckenhoff et al. | 128/760 |
| 4,788,971 | 12/1988 | Quisno | 604/289 |
| 4,820,490 | 4/1989 | Morris | 422/58 |
| 4,837,373 | 6/1989 | Gunkel et al. | 422/56 |

OTHER PUBLICATIONS

"The Quantitative Gravimetric Determination of Sebum Production", John S. Strauss, M.D. and Peter E. Pochi, M.D., vol. 36, pp. 293-298, (1961).

"Comparative Effect of Isotretinoin and Etretinate on Acne and Sebaceous Gland Secretion", Jay A. Goldstein, M.D., et al., vol. 6, No. 4, pp. 760-765, Part 2, (Apr. 1982).

"Failure of Benzoyl Peroxide to Decrease Sebaceous Gland Secretion in Acne", Jay A. Goldstein and Peter E. Pochi, Dermatologica 162:287-291, (1981).

"Sustainable Rates of Sebum Secretion in Acne Patients and Matched Normal Control Subjects", Holly Hake Harris, B. S. et al., Am Acad. Dermatol, pp. 200-203, (1983).

Primary Examiner—Max Hindenburg
Attorney, Agent, or Firm—Fish & Richardson

[57] ABSTRACT

A sampling device and method for collection of sebum secreted by a person for determination of the person's skin oil characteristics includes a sampling element having a backing member of liquid impervious material. An absorbent material is disposed upon the backing member for absorbing sebum secreted by a person's skin, the absorbent material defining an absorption surface. A device is provided for disposing the absorption surface in contact with a region of the person's skin during the predetermined sampling period. The element is sealed within a liquid impervious pouch formed at least in part of the backing member during transport of the collected sebum to a site for measurement. A method for collection of sebum for selection of facial cosmetics of complementary formula is also described, including the step of providing a line of facial cosmetics formulated with oil and the like present at stepped levels preselected to complement a range of sebum production.

11 Claims, 1 Drawing Sheet

U.S. Patent  Jan. 1, 1991  4,981,145
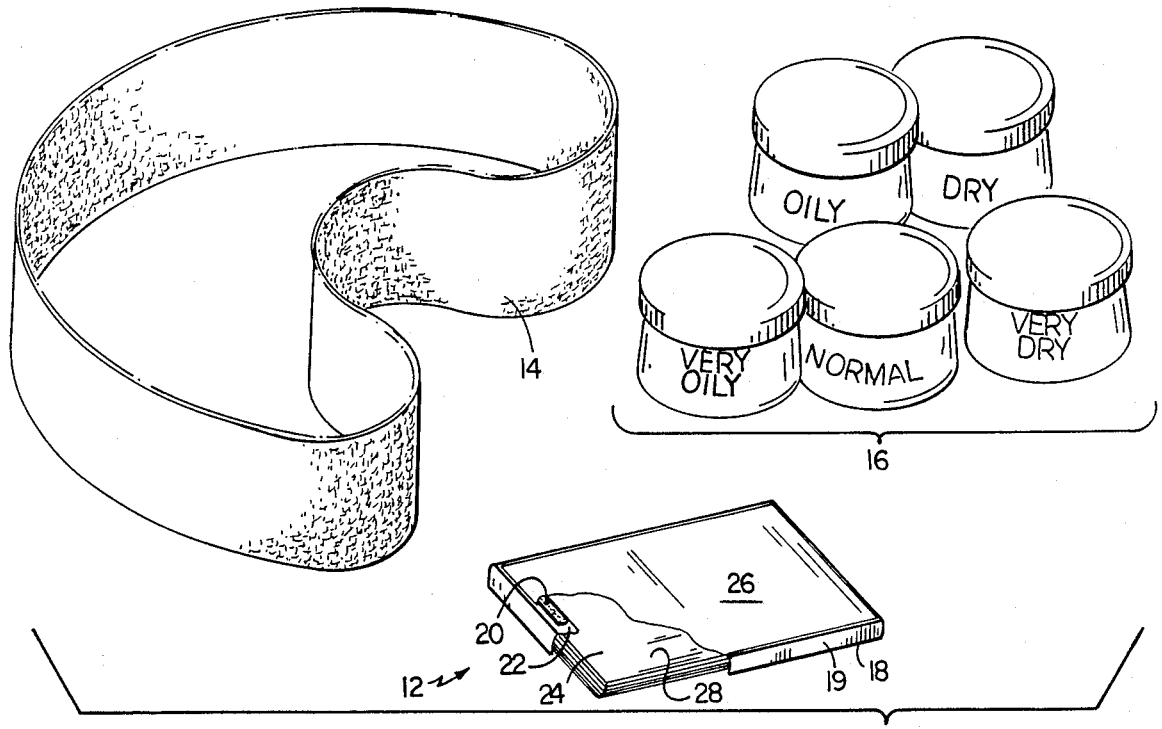
FIG.1
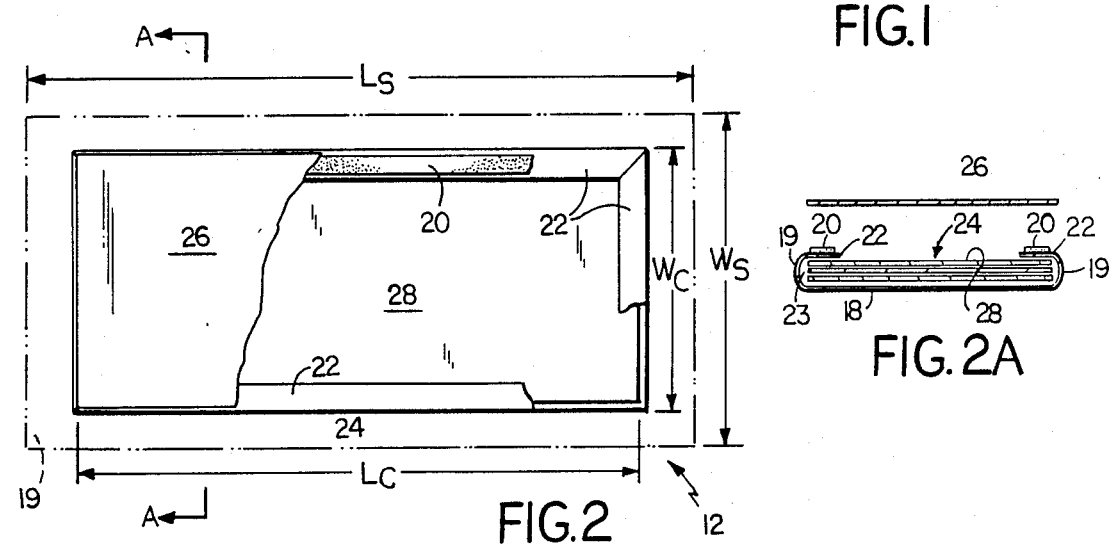
FIG.2
FIG.2A
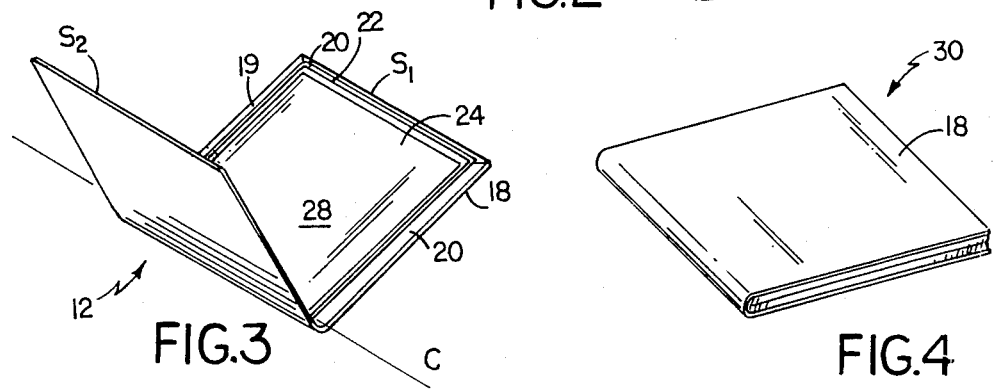
FIG.3
FIG.4

METHOD AND APPARATUS FOR DETERMINING SEBUM PRODUCTION FOR SELECTION OF COSMETICS OF COMPLEMENTARY FORMULATION

BACKGROUND OF THE INVENTION

The invention relates to determination of a person's sebum secretion level for selection of facial cosmetics of complementary formulation.

It has been observed that the rate at which sebum, i.e. skin oil, is produced and secreted upon the surface of the skin varies from person to person. As a result, facial cosmetics formulated for skin with average sebum production, i.e. so-called "normal" skin, are not suited for use by a person with lower or higher sebum production, i.e. so-called "dry" or "oily" skin. It has beer thought to adjust facial cosmetic formulations to accommodate different levels of sebum production by varying the level of oil and the like, i.e. mineral oil, petrolatum, glycerine, etc., in the formulation to compensate for skin oil secretion, e.g. formulas having lower levels of oil and the like, or oil-free formulas, may be provided in cosmetics labelled for persons with "oily" skin. Cosmetics labelled as being formulated for "dry" skin may include relatively higher levels of oil and the like to help moisturize and protect the skin. The terms "very oily" and "very dry" have also been used.

Others have sought to quantify sebum production. For example, Strauss and Pochi, writing in *The Journal of Investigative Dermatology* (Vol. 36, 1961), described a procedure for quantitative gravimetric determination of sebum production. Tur et al. U.S. Pat. No. 3,906,933 describes a device for determining skin type, on the basis of sebum content of the skin, and skin surface topography by microscopic examination of an electrostatically charged printing stamp. Miller U.S. Pat. No. 4,532,937 describes a sebum collection device consisting of an open-celled, microporous, hydrophobic polymeric film applied to the surface of the skin with a thin layer of pressure sensitive adhesive. It is suggested that the level of sebum secretion may be determined by examination of translucent patterns in the film, or by solvent extraction. Hofke et al. U.S. Pat. No. 4,623,793 describes a battery-powered device for determining skin type by measurement of the level of monochromatic light passing through a sample.

SUMMARY OF THE INVENTION

According to one aspect of the invention, a sampling device for collection of sebum secreted by a person for determination of the person's skin oil characteristics comprises a sampling element comprising a backing member comprised of liquid impervious material, and, disposed upon the backing member, means for absorbing sebum secreted by a person's skin, the means for absorbing defining an absorption surface; means for disposing the absorption surface in contact with a region cf the person's skin during a predetermined sampling period; and means for sealing the means for absorbing the sebum within a liquid impervious pouch comprised of the backing member during transport of the collected sebum to a site for measurement.

Preferred embodiments of this aspect of the invention may include one or more of the following features. The means for disposing the absorption surface comprises a headband, preferably the headband defines a skin contacting surface of sebum absorbent material. The sampling element further comprises a band of adhesive extending generally about the perimeter of a first surface of the backing member, the means for absorbing disposed adjacent said first surface. Preferably, the first surface of the backing member defines a circumferential region about the means for absorbing, and the means for sealing comprises the band of adhesive disposed in the circumferential region, the backing member defining an axis dividing the sampling element into a first portion and a second portion, the sampling element adapted to be folded at the axis to close the first portion upon the second portion in a manner to cause the circumferential region of the first portion to overly the circumferential region of the second portion, the adhesive in the circumferential region sealing the means for absorbing within the liquid impervious pouch of the backing member. The means for absorbing is a multi-layer stack of papers. The liquid impervious backing member is comprised of aluminum foil. The sampling device further comprises a cover sheet disposed upon the absorption surface and extending circumferentially therebeyond into engagement with the adhesive to protect the absorption surface and the means for absorbing prior to testing, the cover sheet adapted to be removed prior to collection of sebum.

According to another aspect of the invention, a method for collecting sebum production from a person's skin comprises providing a sampling device, e.g as described above; wearing the headband for a predetermined period to cleanse the skin surface; removing the cover sheet to expose the absorption surface; placing the absorption surface within the headband, in contact with the skin surface; maintaining the contact for a predetermined test period; removing the absorption surface from contact with the skin; folding the sampling element at the axis to engage the adhesive between the opposed portions of the circumferential region thereby sealing the collected sebum within the liquid impervious pouch of the backing member; and transporting the collected sample to a site for determining sebum production.

Preferred embodiments of this aspect of the invention may include one or more of the following features. For selection of facial cosmetics of complementary formula, the method further comprises providing a line of facial cosmetics formulated with oil and the like present at stepped levels preselected to complement a range of sebum production. Preferably the line cf facial cosmetics comprises cosmetics formulated for very oily, oily, normal, dry and very dry skin.

Thus there is provided a system for simply and accurately obtaining measurement cf a person's sebum production rate from a person's skin, and for applying that measurement to select, from a line of facial cosmetics, a cosmetic formulated to complement that person's skin characteristics.

These and other features and advantages of the invention will be apparent from the following description of a presently preferred embodiment, and from the claims.

DESCRIPTION OF A PRESENTLY PREFERRED EMBODIMENT

We first briefly describe the drawings.

FIG. 1 is a somewhat diagrammatic view of the sampling device of the invention;

FIG. 2 is a plan view of the sampling element of FIG. 1, partially in section; while FIG. 2A is a side section view of the element taken at the line 2A—2A of FIG. 2; and FIGS. 3 and 4 are somewhat diagrammatic sequential views of the sampling element being folded to form a pouch for transport of a sample.

A sampling device 10 of the invention consists of sampling element 12, a headband 14 of terry cloth or the like, and a line of cosmetics 16 formulated to complement a segment of the range of skin sebum production characteristic of most of the adult human population.

Referring to FIG. 2, the sampling element 12 consists of a backing member 18 of nonporous material, e.g. aluminum foil or the like, of length $L_s$ and width $W_s$, e.g. 7 cm by 3.5 cm. The perimeter portion 19 of the backing member 18 is folded over, and a band of adhesive 20, about 5 mm wide (only a segment is shown in FIG. 2), extends about the face surface 22 of the perimeter portion 19 of the backing member 18. A sebum collection or absorption member 24, e.g. three layers of absorbent paper such as cigarette paper used for rolling cigarettes, is disposed upon the backing member 18, within the folded over portion 19, with the adhesive band 20 upon surface 22 extending circumferentially thereabout. The collection member is sized, with length $L_c$ and width $W_c$, e.g. 6 cm by about 2.5 cm, to lie beneath the overlap, e.g. by at least about ⅛ inch, of the surface 22 bearing the adhesive band 20, within the region 23 defined by the backing member 18. A releasable cover sheet 26 is disposed over the exposed absorption surface 28 of the collection member, the cover sheet releasably secured in place by its engagement upon the adhesive 20.

A person wishing to select facial cosmetics of formulation complementary to the sebum production rate characteristic of his or her skin obtains a sampling device 10 of the invention. The headband 14 is worn about the head for about 15 minutes in order to absorb skin oils already secreted upon the surface so that, at the end of the period, the surface of the person's forehead is relatively free of skin oils. At the conclusion of this cleansing period, the cover sheet 26 is removed from the sampling element 12 to expose the absorption surface 28 of the collection member 24. The sampling element is placed within the headband 14, with the collection surface 24 in contact with the person's skin, further secured by adhesive 20. After a predetermined collection period, e.g. three hours, the sampling element is removed. Referring to FIG. 3, the sampling element is folded along center-line C, to cause the adhesive 20 about the perimeter of a first portion $S_1$ to engage upon the adhesive about the perimeter of the opposed second portion $S_2$, thereby to seal the collection member 24 within a moisture impervious pouch 30 formed by the backing member 18, with the perimeter portion 19 extending thereabout.

The sampling element pouch may then be mailed to a test laboratory where to backing member 18 is opened and the collection element 24 removed. The sheets of the collection element are inspected visually, and those papers bearing evidence of sebum secretion are analyzed, as described below. (Visualization may be facilitated by holding the papers to the light.)

The amount of sebum collected may be determined using a nominal pre-collection weight for the papers of the collection member 24 where the variation from paper to paper is of the order of about ±2%, or a tare weight may be determined for the papers in advance of sebum sample collection. The papers containing the skin oil are desiccated to remove residual moisture, and then weighed. The pre-collection weight is compared to the final weight in order to determine a relative rate of sebum production.

The person is provided with a recommendation of facial cosmetics from a line of cosmetics 16 formulated with levels of oil and the like appropriate for numerical levels of sebum production, e.g. corresponding to VERY OILY, OILY, NORMAL, DRY and VERY DRY skin characteristics.

Other embodiments are within the following claims. For example, the weight of sebum production may also be determined according to the procedure described by Strauss and Pochi ("The Quantitative Gravimetric Determination of Sebum Production", *The Journal of Investigative Dermatology* (36, 1961) pp. 293–298, the disclosure of which is incorporated herein by reference).

What is claimed is:

1. A sampling device for collection of sebum secreted by a person for determination of the person's skin oil characteristics, comprising
   a sampling element comprising a backing member, adapted for folding and comprised of liquid impervious material, and, disposed upon said backing member, means for absorbing sebum secreted by a person's skin, said means for absorbing defining an absorption surface;
   means for disposing said absorption surface in contact with a region of the person's skin during a predetermined sampling period; and,
   for transport of the collected sebum to a site for measurement, means for sealing said means for absorbing said sebum within a liquid impervious pouch comprised of the folded backing member.

2. The sampling device of claim 1 wherein said means for disposing said absorption surface comprises a headband.

3. The sampling device of claim 2 wherein said headband defines a skin contacting surface of sebum absorbent material.

4. The sampling device of claim 1 wherein said sampling element further comprises a band of adhesive extending generally about the perimeter of a first surface of said backing member, said means for absorbing disposed adjacent said first surface.

5. The sampling device of claim 4 wherein said first surface of said backing member defines a circumferential region about said means for absorbing, and said means for sealing comprises said band of adhesive disposed in said circumferential region, said backing member defining an axis dividing said sampling element into a first portion and a second portion, said sampling element adapted to be folded at said axis to close said first portion upon said second portion in a manner to, cause the circumferential region of said first portion to overly the circumferential region of said second portion, said adhesive in said circumferential region sealing said means for absorbing within said liquid impervious pouch of said backing member.

6. The sampling device of claim 1 wherein said means for absorbing is a multi-layer stack of papers.

7. The sampling device of claim 1 wherein said liquid impervious backing member is comprised of aluminum foil.

8. The sampling device of claim 1 further comprising a cover sheet disposed upon said absorption surface and extending circumferentially therebeyond into engagement with the adhesive to protect said absorption surface and said means for absorbing prior to testing, said cover sheet adapted to be removed prior to collection of sebum.

9. A method for collecting sebum production from a person's skin, comprising:

providing a sampling device for collection of sebum secreted by the person comprising a sampling element comprising a backing member comprised of liquid impervious material, means for absorbing sebum secreted by the person's skin, said means for absorbing defining an absorption surface, a band of adhesive extending generally about the perimeter of a first surface of said backing member, said first surface of said backing member defining a circumferential region about said means for absorbing, said band of adhesive disposed in said circumferential region, said backing member defining an axis dividing said sampling element into a first portion and a second portion, said sampling element adapted to be folded at said axis to close said first portion upon said second portion in a manner to cause the circumferential region of said first portion to overly the circumferential region of said second portion, said adhesive in said circumferential region sealing said means for absorbing within a liquid impervious pouch comprised of said backing member during transport of said sampling element to a site for measurement of sebum collection; a cover sheet disposed upon said absorption surface and extending circumferentially therebeyond into engagement with the adhesive to protect said absorption surface and said means for absorbing prior to testing, said cover sheet adapted to be removed prior to collection of sebum; and a headband for disposing said absorption surface in contact with a region of the person's skin during a predetermined sampling period, said headband defining a skin contacting surface of sebum absorbent material;

wearing said headband for a predetermined period to cleanse the skin surface;

removing said cover sheet to expose said absorption surface;

placing said absorption surface within said headband, in contact with the skin surface;

maintaining said contact for a predetermined test period;

removing said absorption surface from contact with the skin;

folding said sampling element at said axis to engage the adhesive between the opposed portions of the circumferential region thereby sealing the collected sebum within the liquid impervious pouch of said backing member; and transporting said collected sample to a site for determining sebum production.

10. The method of claim 9 for selection of facial cosmetics of complementary formula, comprising the further step of:

providing a line of facial cosmetics formulated with oil and the like present at stepped levels preselected to complement a range of sebum production.

11. The method of claim 10 wherein said line of facial cosmetics comprises cosmetics formulated for very oily, oily, normal, dry and very dry skin.

* * * * *

UNITED STATES PATENT AND TRADEMARK OFFICE
CERTIFICATE OF CORRECTION

PATENT NO.   : 4,981,145
DATED        : January 1, 1991
INVENTOR(S)  : Jay A. Goldstein It is certified that error appears in the above-identified patent and that said Letters Patent is hereby corrected as shown below:

Col. 1, line 17, "beer" should be --been--.

Col. 1, line 59, "cf" should be --of--.

Col. 2, line 49, "cf" should be --of--.

Col. 2, line 53, "cf" should be --of--.

Col. 3, line 22, "!9" should be --19--.

Col. 3, line 43, "cf" should be --of--.

Col. 4, line 54, delete "," after "to".

Signed and Sealed this

Eighth Day of September, 1992

*Attest:*

DOUGLAS B. COMER

*Attesting Officer*     *Acting Commissioner of Patents and Trademarks*